US006595982B2

(12) United States Patent
Sekino et al.

(10) Patent No.: US 6,595,982 B2
(45) Date of Patent: *Jul. 22, 2003

(54) TUBULAR MEDICAL DEVICE

(75) Inventors: Masaki Sekino, Shuzuoka-ken (JP); Shin Maki, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/131,071

(22) Filed: Apr. 25, 2002

(65) Prior Publication Data
US 2002/0115983 A1 Aug. 22, 2002

Related U.S. Application Data

(62) Division of application No. 08/867,508, filed on Jun. 2, 1997.

(30) Foreign Application Priority Data

Jun. 3, 1996 (JP) .............................................. 8-140072

(51) Int. Cl.⁷ .............................................. A61M 25/00
(52) U.S. Cl. ..................... 604/524; 604/95.05; 600/149
(58) Field of Search .......................... 604/93.01, 95.01, 604/95.05, 523, 524, 526, 527; 600/139, 146, 149

(56) References Cited

U.S. PATENT DOCUMENTS

| | | | |
|---|---|---|---|
| 5,199,950 A | 4/1993 | Schmitt et al. | |
| 5,255,668 A | 10/1993 | Umeda | |
| 5,395,328 A | 3/1995 | Ockuly et al. | |
| 5,399,164 A | 3/1995 | Snoke et al. | |
| 5,472,017 A | 12/1995 | Kovalcheck | |
| 5,484,407 A | 1/1996 | Osypka | |
| 5,549,542 A | 8/1996 | Kovalcheck | |
| 5,715,817 A | 2/1998 | Stevens-Wright et al. | |

FOREIGN PATENT DOCUMENTS

| | | |
|---|---|---|
| DE | 42 10 645 A1 | 10/1992 |
| EP | 0 630 657 A1 | 12/1994 |
| JP | 4-261635 A | 9/1992 |
| JP | 6-343702 A | 12/1994 |
| WO | WO 94/10897 A1 | 5/1994 |
| WO | WO 95-05771 A1 | 3/1995 |
| WO | WO 96/40344 A1 | 12/1996 |

*Primary Examiner*—Brian L. Casler
*Assistant Examiner*—Jeremy Thissell
(74) *Attorney, Agent, or Firm*—Burns, Doane, Swecker & Mathis, LLP

(57) ABSTRACT

A tubular medical device comprises a tubular body, a lumen, a compression-resisting member inserted in the lumen so that it cannot move in the direction of the axis of the tubular body, with its distal end located at a predetermined distance from the distal end of the tubular body toward the proximal end, a pull wire whose distal end is secured near the distal end of the tubular body at a position deviated from the axis of the tubular body and which is led in the tubular body to the proximal end of the tubular body, and a pulling mechanism for pulling the pull wire toward the proximal end of the tubular body which is attached to the proximal end of the tubular body and has a manipulation dial. The compression-resisting member consists of a main body and a secured portion. The compression-resisting member main body, and has a property of resisting compression in the axial direction of the tubular body. The secured portion retains the main part in place in the lumen.

6 Claims, 6 Drawing Sheets

TUBULAR MEDICAL DEVICE

This application is a divisional application of application Ser. No. 08/867,508, filed on Jun. 2, 1997.

BACKGROUND OF THE INVENTION

This invention relates to a tubular medical device designed for insertion into a body, for example a hollow organ or body cavity (heart, blood vessel, alimentary canal, urethra, abdominal cavity, etc.), for medical examination or treatment, and especially to a tubular medical device used for guiding an endoscope into a hollow organ or body cavity to examine.

Low invasive operations are gradually taking the place of high invasive operations such as incision. Especially, application of endoscopic surgery using an endoscope has rapidly spread in recent year.

Endoscopic surgery was generally in the field of digestive organs. It was then applied to the field of respiratory organ, ear/nose/throat, neurosurgery, obsterics and gynecology, and orthopedics.

A small-diameter endoscope system used for endoscopic surgery comprises a catheter body which is inserted into the body of a patient and a control portion which an operator manipulates by hands. The catheter body is generally provided at the distal end portion with a mechanism which turns the distal end portion in an intended direction in order to make the distal end portion proceed along a curved or branched hollow organ (insertion path) or to view a different part of the organ.

To make the distal end portion of a tubular medical device bendable, a method which connects two or more articulation rings movably in series and bends the distal end by pulling a wire (wires) is used. However, a tubular medical device which does not have articulation rings is proposed to meet the increasing request for a thinner endoscope.

The tubular medical device has a closely wound coil with a compression resistance in the direction of the axis securely held in a lumen extending throughout the entire length of the tubular body except the distal end portion. This tubular medical device has a wire whose distal end is secured near the distal end of the tubular body away from the axis and which is passed through the compression-resisting member or another lumen The distal end portion of this tubular medical device can be bent from outside the body by pulling the proximal end of the wire Japanese Patent Application laid open under No. 94-343702). This tubular medical device is made so that only the distal end portion bends to pull on the wire, by putting a closely wound coil in the tubular body which resists compression in the direction of the axis.

In the manufacturing process of this tubular medical device, a lumen in which the closely wound coil is held is formed in the tubular body, then the closely wound coil is inserted into the lumen to the predetermined position, and the coil is secured in the lumen at some portions (distal end portions and proximal end portion of the coil, for example). To make insertion of the coil into the lumen in this process, the interior diameter of the lumen must be made a little larger than the exterior diameter of the coil, and hence a certain gap is inevitably formed between the inside wall of the lumen and the outside surface of the coil. Because of its very small exterior diameter of the coil and a gap between the inside wall of the lumen and the outside surface of the coil, the coil easily bends in the lumen to a small compressing force except the secured portions.

If the wire is pulled when the coil is thus bending, the pulling force is applied in a direction deviated from the direction axis, the coil bends easily. As the result, not only the distal end portion of the tubular body but also the portion with the coil put in bends, and hence the distal end portion does not bend accurately according to pull on the wire.

SUMMARY OF THE INVENTION

The object of this invention is to solve the above problem, by providing an improved tubular medical device for insertion into a body only the distal end portion of which bends accurately according to the pulling force.

This object is attained by the tubular medical device of this invention which comprises a tubular body, a lumen extending in almost entire length of said tubular body, and a compression-resisting member which is held in said lumen with a distal end positioned at a predetermined distance from a distal end of said tubular body to a proximal side and secured in said lumen so as not to move in a direction of an axis of said tubular body, a wire whose distal end is secured at a position in a wall of said tubular body close to said distal end of said tubular body and displaced from the axis of said tubular body and whose a proximal end is lead out of a proximal end of said tubular body, means for pulling said wire which is provided at the proximal side of said tubular body and operated to control a direction of a distal end portion of said tubular body by said wire. The said compression-resisting member comprises a major component which constitutes an essential part of said compression-resisting member and resists a pressure in a direction of a length and secured portions which are connected to said major component or formed as integrated parts of said major component.

DETAILED DESCRIPTION OF PREFERRED EMBODIMENTS

Figure 1:
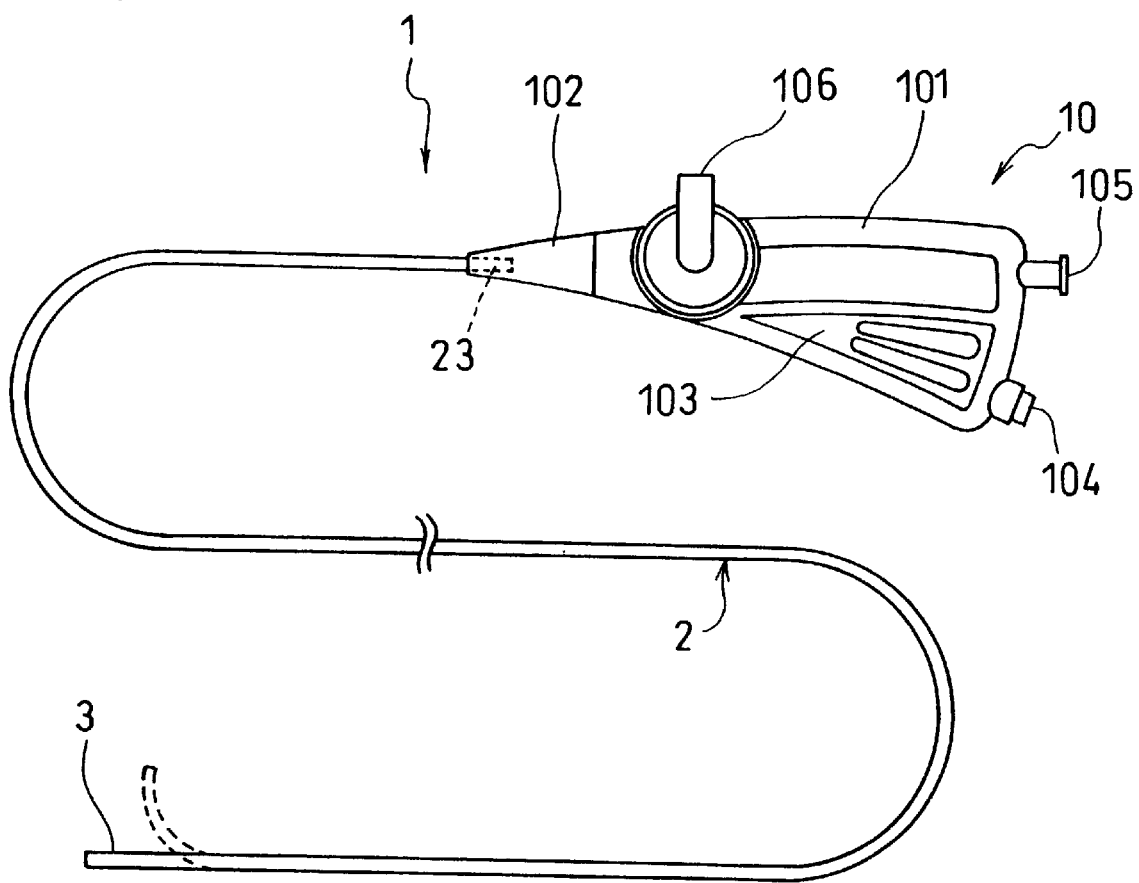
FIG. 1 is a perspective view of the whole body of an embodiment of the tubular medical device of this invention applied to an endoscope (fiberscope).
Figure 2:
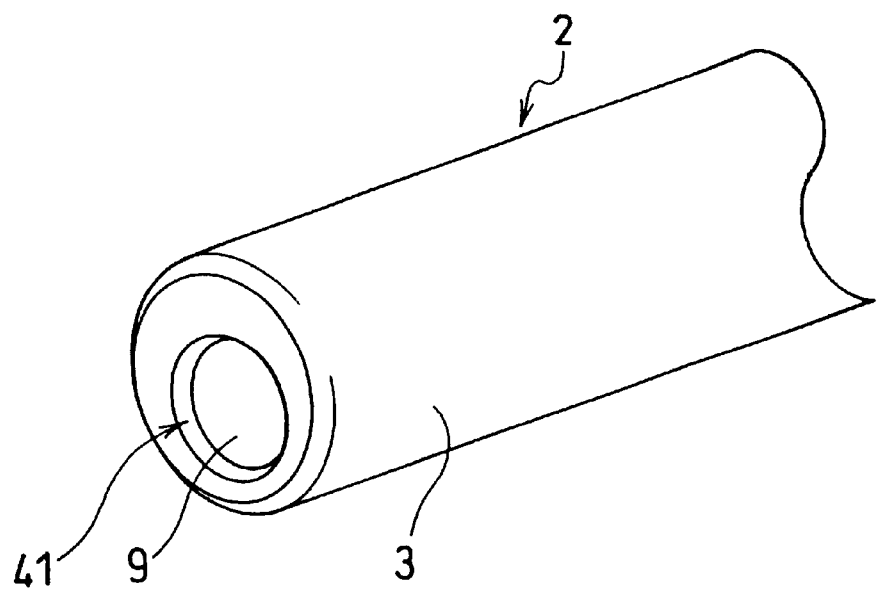
FIG. 2 is a perspective view of the distal end portion of the tubular medical device shown in FIG. 1.
Figure 3:
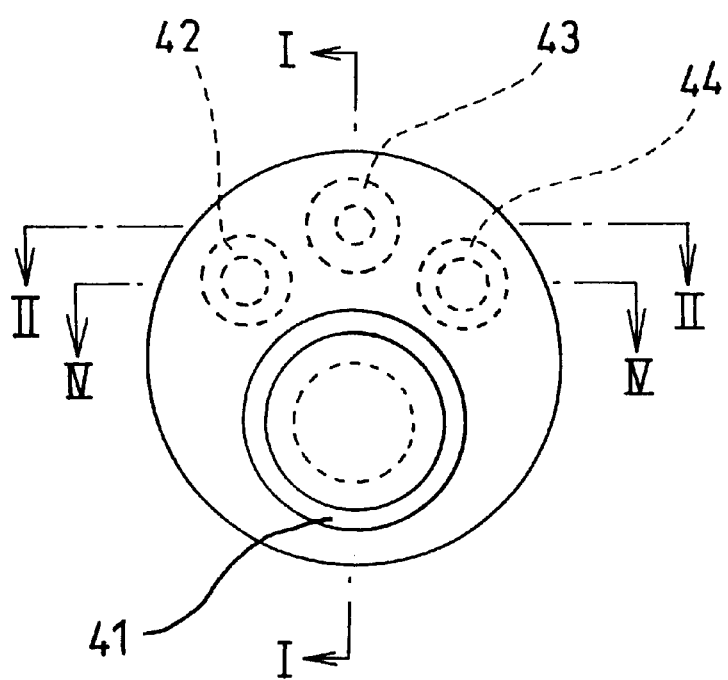
FIG. 3 is a front view of the distal end portion of the tubular medical device shown in FIG. 1.
Figure 4:
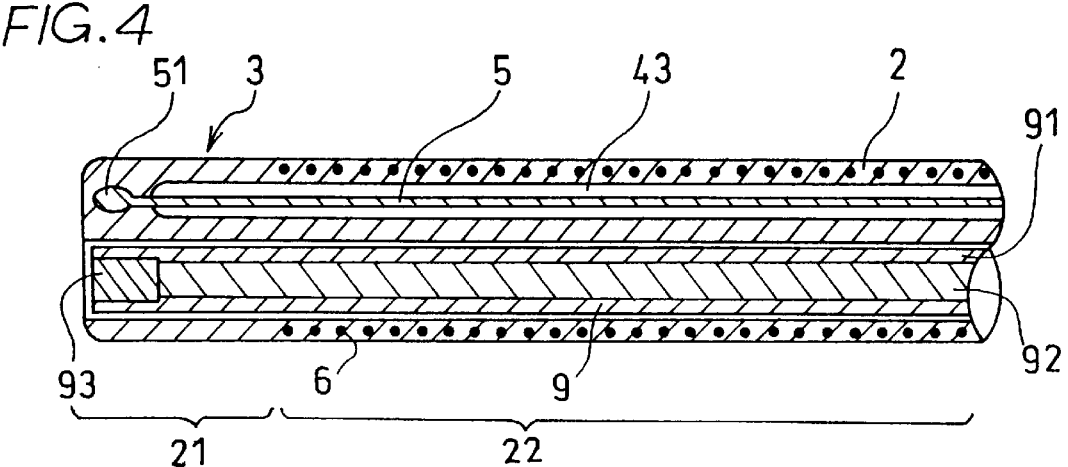
FIG. 4 is a sectional view along line IV—IV in FIG. 3.
Figure 5:
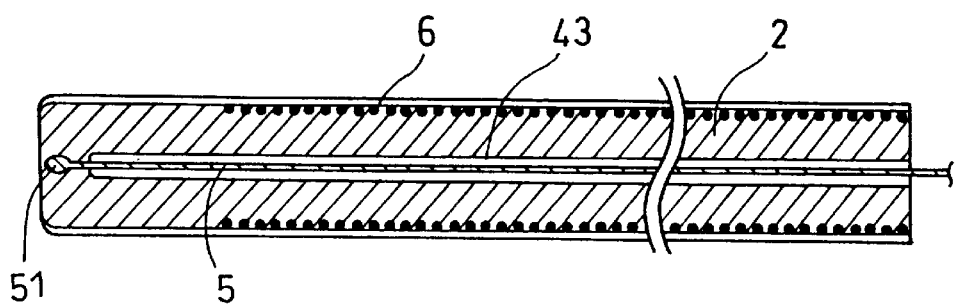
FIG. 5 is a sectional view along line V—V in FIG. 3.
Figure 6:
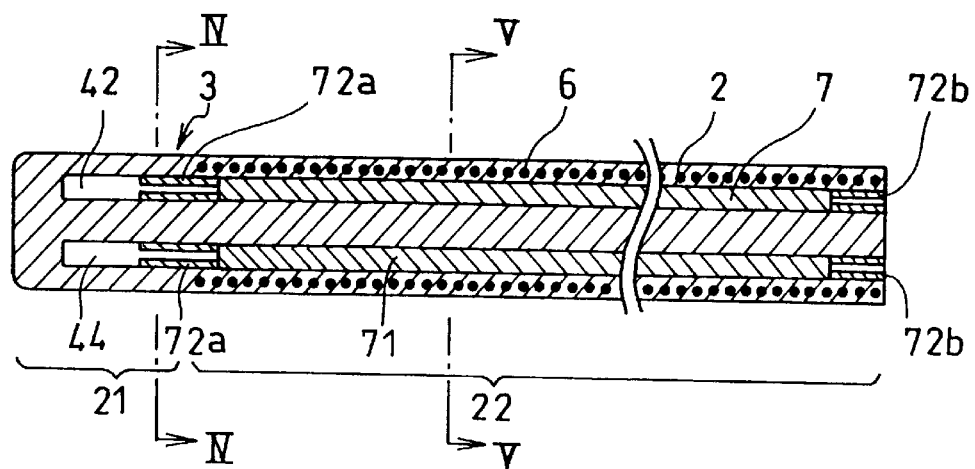
FIG. 6 is a sectional view along line VI—VI in FIG. 3.

Next, the tubular medical device for insertion into a body of this invention is described below in detail with reference to the accompanied drawings. FIG. 1 is a perspective view of the whole body of an embodiment of the tubular medical device of this invention which is applied to an endoscope (fiberscope). FIG. 2 is a perspective view of the distal end portion of the tubular medical device shown in FIG. 1. FIG. 3 is a front view of the distal end portion of the tubular medical device shown in FIG. 1. FIG. 4 is a sectional view along line IV—IV in FIG. 3. FIG. 5 is a sectional view along line V—V in FIG. 3. FIG. 6 is a sectional view along line VI—VI in FIG. 3.

In the following description, the right side end of the endoscope is referred to as the proximal end, and the left side end as the distal end.

The tubular medical device 1 of this invention is a tubular medical device for insertion into hollow organs, for example blood vessel, and may also be called a catheter tube.

The tubular medical device 1 for insertion into a body comprises a tabular body 2, a lumen 42 extending in the almost entire length of the tubular body 2, an compression-resisting member 7 inserted in the lumen 42 so that it cannot move in the direction of the axis of the tubular body 2, with its distal end located at a predetermined distance from the distal end of the tubular body 2 toward the proximal end, a pull wire 5 whose distal end is secured near the distal end of the tubular body 2 at a position deviated from the axis of the tubular body 2 and which is led in the tubular body 2 to the proximal end of the tubular body 2, and a pulling mechanism for pulling the pull wire 5 toward the proximal end of the tubular body which is attached to the proximal end of the tubular body 2 and has an manipulation dial 106.

The tubular medical device 1 is constructed so that the distal end portion (deformable portion) 21 of the tubular body 2 bends when the pull wire 5 is pulled toward the proximal end of the tubular body 2. The compression-resisting member 7 consists of a main body (major portion) 71 and a secured portion 72 as shown in FIGS. 6 to 10. The compression-resisting member main body 71 constitutes an almost entire part of the compression-resisting member 7, and has a property of resisting compression in the axial direction of the tubular body 2. The secured portion may be attached to the main body 71 or formed as one single part together with the main body 71. The secured portion retains the main part 71 in place in the lumen 42 The main body 71 (major component) of the compression-resisting member 7 is formed of a long cylindrical or long substantially cylindrical member.

As shown in FIGS. 1 to 9, the tubular medical device 1 of this invention has a tubular body 2. The tubular body 2 is formed of a polymer such as soft polyvinyl chloride, polyethylene, polypropylene, polyurethane, polyamide, polytetrafluoroethylene, silicone rubber, or ethylene-vinyl acetate copolymer.

It is preferable to provide the tubular body 2 partly or entirely with a radiopaque property so that the tubular device is visible under fluoroscopy. This can be attained by adding a radiopaque substance such as barium sulfate, bismuth oxide, or tungsten to the material of the tubular body 2 or embedding a marker made of a radiopaque substance as described above in the tubular body 2 or attaching the maker to the surface of the tubular body 2, for example.

Further, to improve the slidability against a hollow organ, the outside surface of the tubular body 2 may be coated with a friction-reducing substance such as a hydrophilic polymer (maleic anhydride copolymer, for example) or a fluororesin (polytetrafluoroethylene, for example).

At the distal end portion 3 of the tubular body 2, a deformable portion (or bendable portion) 21 which bends according to later described wire pulling manipulation is formed. To the proximal end 23 of the tubular body 2, a manipulation grip 10 for making manipulation of bending the deformable portion 21 is attached. The middle part 22 of the tubular body 2 between the deformable portion 21 and the proximal end 23 has a certain flexibility such that, when the tubular medical device 1 is inserted into a hollow organ such as a blood vessel or the pancreatic duct, it bends following curved and angular parts of the hollow organ, but does not bend to later described wire pulling manipulation.

A first lumen 42, second lumen 44, third lumen 43, and fourth lumen 41 are formed in the tubular body 2 through its almost entire length as shown in FIG. 6.

The fourth lumen 41 extends from the proximal end to the distal end of the tubular body 2 and is open in the distal end of the tubular body 2 as shown in FIG. 2. This is, the fourth lumen 41 has an open end in the distal end of the tubular body 2.

The first lumen 42, second lumen 44, and third lumen 43 extend from the proximal end of the tubular body 2 to near the distal end of the tubular body 2, with their distal end at a predetermined small distance from the distal end of the tubular body 2 toward the proximal side as shown in FIGS. 5 and 6. The distance between the distal end of the tubular body 2 and that of these lumens 42, 44, and 43 is preferably within the range of 1 to 2 mm.

A fiber optics (a bundle of optical fibers) 9 for viewing inside the hollow organ into which the tubular medical device 1 is inserted is held in the fourth lumen 41. The fiber optics 9 is also used for medical treatment such as applying laser light to the inside wall of a hollow organ.

Figure 8:
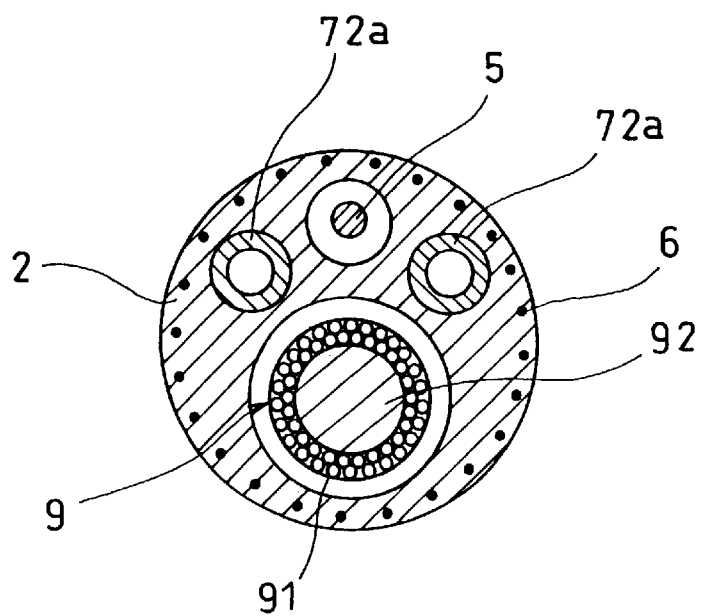
FIG. 8 is a sectional view along line IV—IV in FIG. 6.
Figure 9:
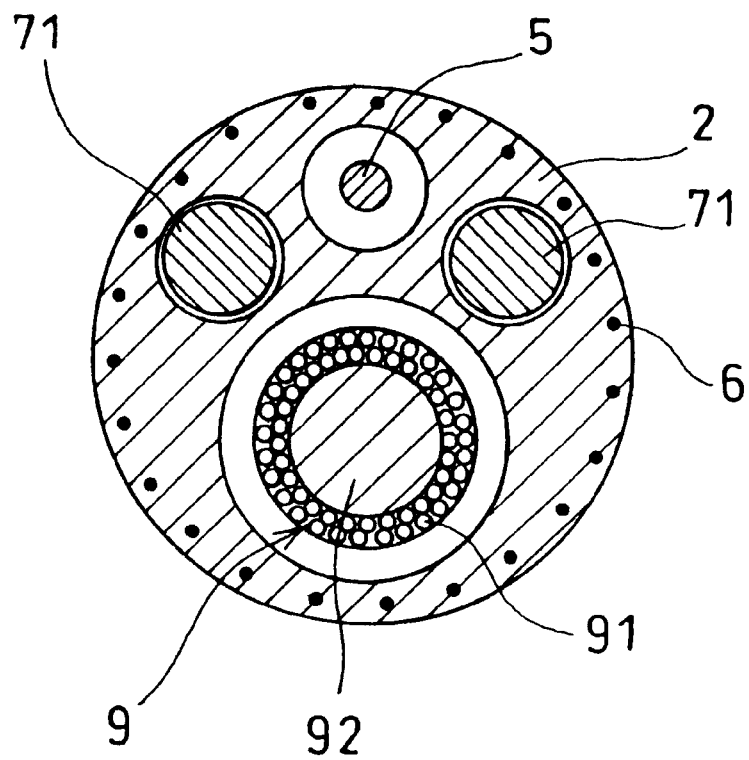
FIG. 9 is a sectional view along line IX—IX in FIG. 6.

The fiber optics 9 consists of light transmitting optical fibers (light guide) 91 and light receiving optical fibers (image guide) 92 as shown in FIGS. 4, 8 and 9. The fiber optics 9 is fabricated by embedding these optical fibers in a resin such as an epoxy resin, acrylic resin, or silicone rubber into a bundle. The light transmitting and receiving optical fibers 91 and 92 consist of optical fibers made of quartz glass, multicomponent glass, or plastic.

The fiber optics 9 is equipped with a lens 93 for collecting the light reflected from an examined area in the distal end of the fiber optics 9, and the lens 93 is located near the opening of the distal end of the lumen 41 as shown in FIG. 4. Although the fiber optics 9 is preferably fixed to the lumen 41, it may be slidable to the lumen 41 so that the distal end portion of the fiber optics 9 can be protruded from and retracted into the distal end opening of the lumen 41.

The light generated by a light source (not shown) at the proximal side (right side in FIG. 1) of the manipulating grip 10 is guided by the light transmitting optical fibers 91 and emitted from the distal end of the light transmitting optical fibers 92 to an examined area of the inside wall of an organ. The light reflected from the inside wall of the organ is collected by the lens 93 and enters the light receiving optical fibers 92 from the distal end. The light is then guided by the light receiving optical fibers 92 to an image display device (not shown) at the proximal side of the manipulating grip.

When there is a space left between the lumen 41 and the fiber optics 9, it is possible to inject fluids into or withdraw body fluids from an hollow organ through the space.

Especially when the fiber optics 9 is held in the lumen 41 without fixing, it is easy to inject fluids into or withdraw body fluids from a hollow organ through the space. Specifically, the lumen 41 can be used to inject medical fluids into the hollow organ in which the tubular medical device 1 is inserted and left. The lumen 41 can also be used as a flashing channel to inject a transparent liquid (physiological salt solution or a solution of grape sugar, for example) for washing away body fluids such as blood and bile obstructing the view when examining the interior of a hollow organ by an endoscope. Further, the lumen 41 can be used as a channel to pass a guide wire and devices for treatment or test such as forceps, cytological diagnosis brush, injection needle, lithodialysis probe which radiates high frequency electromagnetic waves, ultrasonic waves, or water pressure shock waves for breaking a blood stone, and various types of sensors and their lead wires.

The first lumen 42 and the second lumen 44 are used for holding an compression-resisting member 7 for preventing the middle part 22 and proximal end portion 23 of the tubular body 2 from bending to the pulling force to manipulate the deformable portion 21. The third lumen 43 is used to hold the wire 5 for bending the deformable portion 21.

These lumens 42, 43, and 44 are disposed near the circumference of the cross section of the tubular body 2, close to each other, with the third lumen 43 between the first and second lumens 42 and 44 as shown in FIGS. 8 and 9. In other words, these lumens are disposed so that the distance between the first lumen 42 and the second lumen 44 is greater than the distance between the first lumen 42 and the third lumen 43 and that between the second lumen 44 and the third lumen 43.

Figure 10:
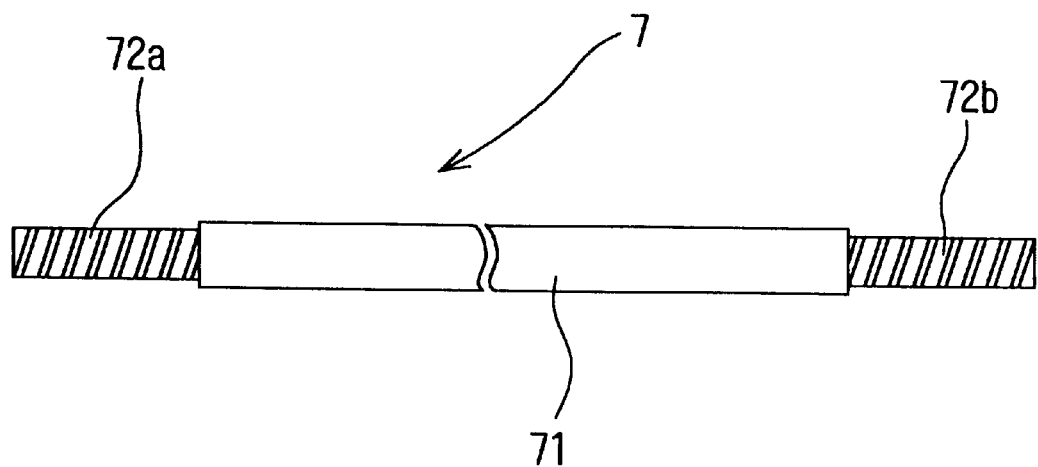
FIG. 10 is an enlarged perspective view of a compression-resisting member used in the tubular medical device of this invention.

The distal ends of the lumens 42, 43, and 44 are dosed. A compression-resisting member 7 is set in the portion of the lumens 42 and 44 located in the middle portion 22 and proximal portion 23 of the tubular body 2 as shown in FIG. 6. The compression-resisting members 7 can also be called as compression-resisting supports. Each compression-resisting member 7 comprises a main body 71 which is not compressible in the direction of the axis (length). These main bodies 71 of the compression-resisting members have secured portions 72a, 72b (or means for fixing the main body to the wall of the lumen), which are coils of a strip (flat wire) closely wound in a spiral substantially with a small gap between adjacent turns attached to their distal and proximal ends of each of main body 71 as shown in FIG. 10. The coils may be made separately and attached to the main body 71, or may be formed as a single part together with the main body 71. The main bodies 71 of the compression-resisting members 7 are substantially not compressible in the direction of their length, and prevent the tubular body 2 from bending to the compressing force applied when the wire 5 is pulled. The main body 71 (major component) of the compression-resisting member 7 is formed of a long cylindrical member.

In this embodiment, the main body 71 of the compression-resisting members 7 is a solid wire, as shown in an enlarged view in FIGS. 6 and 10. The compression-resisting members 7 are placed in the lumens 42 and 44 so that their main body 71 is positioned in the middle portion 22 of the tubular body 2. These main bodies 71 are provided with the secured portions 72a, 72b which are closely wound coils of a flat wire at their distal and proximal ends.

The main bodies 71 of the compression-resisting members 7 are made of a material which is not compressed in the direction of the length and have an appropriate flexibility to bend a certain amount. For the material, stainless steel (austenitic stainless steel such as SUS304, SUS316, and SUS312; mulaging stainless steel; and precipitation hardening stainless steel, etc.), super elastic alloy (Ni—Ti alloy, etc.), Cu—Zn alloy, copper alloy (Cu—Sn, etc.), carbon steel, tungsten steel, various elastic metals (aluminium, platinium, etc.), and various hard resins (polyamide, polyethylene, polypropylene, poly allylate, poly(vinyl chloride), polytetrafluoro-ethylene, polyester, polyimide, etc.) can be used. austeritic stainless steel and super elastic alloy are preferable. By forming the compression-resisting member main body 71 of any of these materials, the middle portion 22 of the tubular body 2 has an appropriate flexibility which makes insertion of the tubular medical device 1 into a hollow organ such as a blood vessel easy.

The compression-resisting member main body 71 must not be a solid wire as shown in the Figures, and may be a hollow tube or pipe compression-resisting in the direction of the axis. When such a tube or pipe is used, the above described materials are preferable for the material of the tube or pipe.

The secured portions 72a and 72b of this embodiment consist of a closely wound coil as shown in FIG. 10, respectively. A strip (or a wire) is closely wound on the outside surface of the secured portions 72 so that there is a small gap between adjacent turns. As the result, the secured portions 72 have unevenness formed by the gaps.

The secured portions 72a of the first and second compression-resisting members are positioned at or near the boundary 24 of the deformable portion 21 and the middle portion 22 of the tubular body 2 and fixed to the inside surface of the lumens 42 and 44 as shown in FIG. 6. On the other hand, the secured portions 72b of the first and second compression-resisting members are positioned near the proximal end 23 of the tubular body 2 and fixed to the inside surface of the lumens 42 and 44.

Fixing of the secured portions 72a and 72b to the inside surface of the lumens 42 and 44 can be made by the following method, for example. First, the compression-resisting members 7 are inserted into the lumens 42 and 44. Next, heat-shrinking tubes (not shown) are put on the tubular body 2 so as to cover the outside surface of the boundary region 24 and the proximal end portion 23. Then, heat is applied to the heat-shrinking tubes to shrink them, and the shrunk tubes squeeze the tubular body 2. Because of this squeezing force, the inside wall of the lumens 42 and 44 is pressed to the secured portions 72a and 72b, and enters the gaps in the coils. As the result, the secured portions 72a and 72b are firmly held by the inside wall of the lumens 42 and 44.

By thus using coils as the secured potions 72, the compression-resisting members can be fixed in the lumens easily with a high reliability.

The positions where secured portions 72 are attached to (or formed on) the main body 71 of the compression-resisting members 7 are not limited to the distal and proximal ends. For example, one or more secured portions may be attached to (or formed on) the middle portion of the main body 71. However, it is preferable to attach (or form) two secured portions 72 to (or on) the distal and proximal ends of the main body 71 and fix the compression-resisting members 7 at both ends as in the above embodiment.

The secured portions 72 may be fixed in the lumens by other methods. For example, the secured portions 72 can be fixed in the lumens by putting squeezing sleeves (tubular pieces) which can be tighten by caulking on the tubular body 2 and caulking the sleeves. By the squeezing pressure of the caulked sleeves, the inside wall of the lumens is pressed to the outside surface of the secured portions 72 and enters the gaps in the winding of the coils.

Further, an adhesive agent (filler) may be applied between the outside surface of the secured portions 72 and the inside surface of the lumens 42, 44 to increase the reliability of fixing.

Connection of the secured portions 72 to the compression-resisting member main body 71 can be made by bonding each secured portion 72 and the main portion 71 end to end with an adhesive agent (filler). The connection can also be made by forming the distal and proximal end portions of the main body 71 smaller in diameter, inserting each thinner portion into the opening of the coil of a secured portion, and bonding the outside surface of the thinner portion and the inside surface of the coil with an adhesive (filler).

Further, in the tubular medical device of this embodiment, the lumens 42 and 44 are extended to in the deformable portion 21, and the region of the lumens 42 and 44 between their distal end and the distal-side end of the secured portion 72a is left vacant. In other words, the tubular medical device 1 has hollow spaces which extend in the bendable portion 21 as shown in FIG. 6. Therefore, the deformable portion 21 can be bent easily by pulling the wire.

The dimensions such as the exterior diameter of the compression-resisting member main body 71 vary according to the conditions such as the material of the main body 71 and the shape, dimensions of the cross section, and material of the tubular body 2. When a circular stainless steel wire is used for the compression-resisting member main body 71, the exterior diameter is preferably within the range of 0.05 to 1.0 mm, and more preferably 0.3 to 0.35 mm The interior diameter of the lumens 42 and 44 is preferably about 1.2 to 2.0, more preferably about 1.01 to 1.4 times the exterior diameter of the compression-resisting member main body 71. If the interior diameter of the lumens 42 and 44 is larger than 1.0 time the exterior diameter of the compression-resisting member main body 71, insertion of the compression-resisting member main bodies 71 into the lumens 42 and 44 is easy. If the interior diameter of the lumens 42 and 44 is smaller than twice the exterior diameter of the compression-resisting member main body 71, the exterior diameter of the tubular body 2 does not become too large, and the compression-resisting member main bodies 71 do not bend sinuously too much in the lumens 42 and 44. Further, the middle portion 22 of the tubular body 2 does not buckle when the wire 5 is pulled to the proximal side.

There is an appropriate range for the ratio of the secured portions 72 to the overall length of the compression-resisting member 7. If this ratio is too small (the length of the secured portions is too short), the fixing force is not sufficient. If this ratio is excessively large (the length of the secured portions is ), fixing work for a larger part of the compression-resisting member 7 is required and the manufacturing process becomes complicated.

The ratio of the secured portions 72 to the overall length of the compression-resisting member 7 is within the range of about 0.1% to 10%, more preferably about 0.6% to 1.0%. Specifically, the ratio of the length of each secured portion to the length of the compression-resisting member 7 is within the range of about 0.1% to 10%, more preferably about 0.6% to 1.0%. Therefore, the ratio of the length of the two secured portions 72a and 72b to the length of the compression-resisting member 7 is within the range of about 0.2% to 20%, more preferably about 1.2% to 2.0%.

Figure 11:
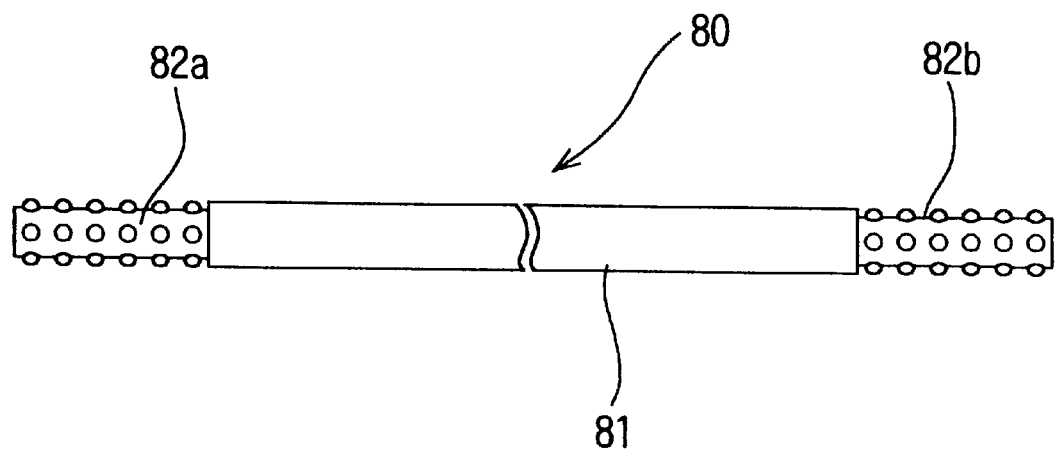
FIG. 11 is an enlarged perspective view of an another compression-resisting member used in the tubular medical device of this invention.

The secured portions may also be the one as shown in FIG. 11. In the compression-resisting member 80 shown in FIG. 11, the outside surface of the distal and proximal end portions of a wire (or tube) of the main body 81 is made rough. The distal and proximal end portions with the roughened surface serve as secured portions 82a and 82b. Roughening of the surface can be performed by rasping the surface with a file or cutting it with laser light.

Since the compression-resisting member 80 of this structure has the secured portions 82a and 82b and the compression-resisting member main body 81 formed together and hence has no joints of the secured portions 82a and 82b and the compression-resisting member main body 81, it does not have the problems with the above described compression-resisting member 80 that the secured portions 82a and 82b can come off from the compression-resisting member main element 81 and that the compression-resisting member 80 prone to bend at the joints (boundaries).

In addition to randomly formed projections and recesses as shown in FIG. 11, grooves or ridges in spirals, circles, or other shapes may be formed on the surface of the secured portions though not shown in Figures.

Figure 7:
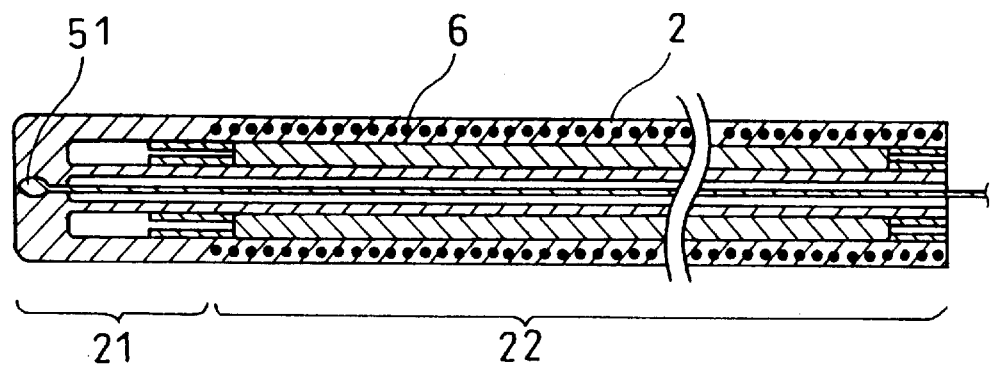
FIG. 7 is a diagrammatic view showing the structure in cross-section of the tubular medical device.

A wire 5 for pulling the deformable portion 21 to bend is extended through the third lumen 43 as shown in FIGS. 4, 5 and 7. The distal end 51 of the wire 5 is buried in the wall of the tubular body 2 between the distal end of the tubular body 2 and that of the lumen 43 to fix to the deformable portion 21. The distal end 51 of the wire 5 is fixed in dose vicinity to the distal end of the tubular body 2 without being exposed in the distal end of the tubular body 2.

The wire 5 is held in the third lumen 43 whose the distal end is secured at a position close to the distal end of the tubular body 2. The wire 5 is displaced from the axis of the tubular body 2 and whose a proximal end is lead out of a proximal end of said tubular body 2. The wire 5 is set in the manner of a off-center arrangement for the tubular body 2 (the axis of the tubular body 2).

The distal end 51 of the wire 5 is fixed at a position away from the center in the cross section of the tubular body 2. Specifically, the distal end 51 of the wire 5 is fixed at a position near the circumference. When the wire 5 is pulled to the proximal side, the deformable portion 21 bends to the side (with respect to the center axis) where the distal end of the wire 5 is fixed.

For the wire 5, a wire which has an adequate strength and durability not to break from many times of frequent pulls and releases along with a high extensional rigidity is preferable. For the material of the wire 5, metal wire (stainless steel wire, super elastic alloy wire, etc.), high tensile strength resin fiber (polyamide, polyethylene, polyallylate, polyester, polyimide, etc.), or carbon fiber, in singe or strand, can be used.

The exterior diameter of the wire varies according to the conditions such as the material of the wire and the shape, dimensions (of the cross section) and material of the tubular body 2. When a polyallylate fiber strand or a single stainless steel wire is used for the wire 5, for example, the exterior diameter of the strand or the wire is within the range of preferably 30 to 500 μm, especially 50 to 300 μm.

As known from the above description, unlike the tubular medial device disclosed in Japanese Patent Application laid open under No. 94-343702, the tubular medical device 1 of this embodiment has a structure which encases the compression-resisting members 7 and the pull wire 5 separately in different lumens. By this structure, the compression-resisting members, the pull wire, and the lumens for encasing them can be made smaller in diameter. As the result it becomes possible to reduce the exterior diameter of the tubular medical device 1.

Since the tubular medical device of this invention has the structure as described above, it can be made thin less than or smaller than 2 mm in exterior diameter, especially 1.0 mm to 1.8 mm in exterior diameter. It is because the tubular medical device of this invention has the above structure that its distal end portion can be bent as desired though being a micro-tube.

It is preferable that the first lumen 42 and the second lumen 44 for encasing the compression-resisting members 7 are disposed in close vicinity of the third lumen 43 for encasing the wire 5. Specifically, the distance between the first lumen 42 and the third lumen 43 and that between the second lumen 44 and the third lumen 43 (the distance here is the thickness of the wall of the tubular body 2 between the lumens) are preferably 0.2 mm or smaller, more preferably within the range of about 0.1 to 0.2 mm. If the distance between the first lumen 42 and the third lumen 43 and that between the second lumen 44 and the third lumen 43 are within this range, the middle portion 22 does not bend easily to the pulling force by the wire 5, and only the deformable portion 21 bends accurately according to the pulling force applied to the wire 5.

Although one lumen for the compression-resisting member 7 suffices for the purpose of this invention, it is preferable to form two lumens for the compression-resisting member 7 with the lumen 43 for the wire 5 between, as shown in the FIGS. 8 and 9. Here, that the first and second lumens 42 and 44 are formed with the third lumen 43 between means that the distance between the first lumen 42 and the second lumen 44 is greater than the distance between the first lumen 42 and the third lumen 43 and that between the second lumen 44 and the third lumen 43, not that the third lumen 43 is literally between the first and second lumens.

By thus disposing three lumens, the components of the force applied by the wire 5 to the distal end of the compression-resisting members 7, which cause the compression-resisting members 7 to bend toward each other, cancel each other. Therefore, the middle portion 22 of the tubular body 2 does not bend, and only the deformable portion 21 bends in the plane passing the center axis of the tubular body 2 and the axis of the wire 5 accurately according to the pulling force applied to the wire 5.

Further, by placing the compression-resisting members and the wire in separate lumens and disposing these lumens near the circumferential surface of the tubular body 2 in dose vicinity to each other, the exterior diameter of the tubular body 2 can be decreased. The tubular medical device 1 of this invention therefore can be inserted into a thinner hollow organ.

Further, in the tubular medical device of this embodiment, the fourth lumen 41, which is the main lumen, is formed eccentrically to the tubular body 2 at a position away from the axis of the tubular body 2 near the circumferential surface as shown in FIGS. 8 and 9. By thus forming the fourth lumen 41, the thickness of the wall of the tubular body 2 around the fourth lumen 41 is not uniform, and the thickest part and thinnest part are formed between the fourth lumen 41 and the circumferential surface of the tubular body 2. The third lumen 43 is formed in the center of the thickest part. As the result, the line connecting the center of the fourth lumen 41 and that of the third lumen 43 passes the center of the tubular body 2. The first lumen 42 and the second lumen 44 are formed in the thick parts of the wall at different sides of the third lumen 43 with the third lumen 43 between, each of them in dose vicinity of the third lumen 43. By thus forming the first to third lumens, the wall of the tubular body 2 (not used by the fourth lumen 41) can be used effectively, and hence the exterior diameter of the tubular body 2 can be reduced.

A tubular reinforcement 6 is embedded in the circumferential part of the wall of the tubular body 2 in at least the proximal end portion 23 and the middle portion 22 so as to enclose the lumens 41 to 44 as shown in FIGS. 4 to 9. This reinforcement 6 may be extended to the middle part of the deformable portion 21. By this structure, the flexural rigidity of the deformable portion 21 can be adjusted so that it decreases toward the distal end. Specifically, by extending the reinforcement 6 to the proximal portion of the deformable portion 21, the distal end portion of the deformable portion 21 can be made more flexible than the proximal end portion.

For the reinforcement 6, a reinforcement formed of wire or thread of a metal (stainless steel, super elastic alloy, etc.), a resin (polyamide, polyethylene, polypropylene, polyester, polyimide, ABS, etc.), carbon fiber, or glass fiber is preferable. A net formed by braiding any of the above wire or thread is especially preferable.

By addition of this reinforcement 6, the torsional rigidity of the tubular medical device 1 increases, and the turning manipulation of the proximal end is transmitted accurately to the distal end 3. The tubular medical device 1 of this invention therefore has a high motion transmission property required to a tubular medical device both for motion around the axis and for motion in the direction of axis. Further, collapsing or narrowing of the lumens 41 to 44 caused by bending of the tubular body 2, especially sharp bending, can be prevented by the reinforcement 6. Furthermore, the flexural aridity of the deformable portion 21 can be changed in steps by the position to which the distal end of the reinforcement 6 is extended so that the deformable portion 21 bends accurately according to wire manipulation.

The distal end of the reinforcement 6 may be positioned in the region where the secured portions 72a of the compression-resisting members 7 are secured, in the proximal side end portion of the deformable portion 21 as shown in FIGS. 4, 5 and 6. When the distal end of the reinforcement 6 is positioned in this region, the boundary 24 (the proximal side end of the deformable portion 21) is defined by the distal end of the reinforcement 6. The distal end of the reinforcement 6 may also be positioned in the middle portion 22. The secured portions 72a of the compression-resisting members 7 extends to a middle portion of the deformable portion 21. The distal end of the secured portions 72a is positioned in the deformable portion 21. Therefore, a difference in physical properties between the deformable portion 21 and the middle portion 22 of the tubular medical device 1 (the boundary 24 of the deformable portion 21 and the middle portion 22) is small. The tubular medical device is more smooth and effective to manipulate.

A manipulation grip or control block 10 is connected at the proximal side of the tubular medical device 1 as shown in FIG. 1. The manipulation grip 10 has a main body 101. The main body 101 of the manipulation grip 10 has a manifold body 102 formed at the proximal side. The proximal end portion 23 of the tubular body 2 is inserted and secured in the manifold portion 102. The main body 101 has a grip 103 formed at the proximal side. The grip 103 has a connector 104 attached on the proximal side end. A tube for guiding an endoscope (not shown) is connected to the connector 104, and an endoscope is inserted though the tube and the connector 104 into the fourth lumen 41 of the tubular body 2. The grip 103 has a branch which extends obliquely (not shown). A connector 105 is attached on the end of the branch. A tube for injecting a fluid is connected to the connector 105.

A control dial 106 for changing the direction of the deformable portion 21 by the wire 5 is disposed on the main body 101 between the manifold portion and the grip 103. A reel (not shown) is attached to the axis of the control dial 106, and turns together with the control dial 106. The proximal end of the wire 5 is brought out of the proximal end of the third lumen 43, passed inside the main body 101, and wound on the reel. When the control dial 106 is turned once clockwise in FIG. 1, for example, the wire 5 is pulled and the deformable portion 21 bends upward as shown in FIG. 1.

By thus bending the deformable portion 21 of the tubular body 2 in a desired direction, a wide area can be viewed by endoscope. In addition, injection of fluids, suction of body fluids, or various medical treatments can be performed through the lumen 41 on a wide area by a simple dial operation.

The tubular medical device of this invention has been described by the embodiments shown m the drawings. However, the tubular medical device of this invention is not limited to the above described structure.

First, the number and disposition of lumens are not limited to those shown in the drawings, and various modifications are possible. For example, modified structures which do not have one or both of the first and second lumens 41 and 44 or ones which have one or more lumens in addition to the first to fourth lumens are included.

Next, although the embodiments shown in the drawings all have one wire, the tubular medical device of the invention may have two or more wires so that the deformable portion 21 of the tubular body 2 can be bent two or more directions. Specifically, two or more lumens (not shown) for encasing wires are formed along the circumference of the cross section of the tubular body 2 at predetermined intervals. Pull wires 5 are inserted in these lumens. And the distal end of each pull wire is secured in the wall of the tubular body 2 at the distal side of the distal end of each lumen. By this structure, the deformable portion 21 can be bent in a desired direction by pulling a single wire or two or more wires simultaneously.

For example, a four wire structure can be embodied by forming four lumens at substantially equal intervals along the circumference of the cross section of the tubular body 2, inserting pull wires 5 in these lumens, and securing the distal end of each wire 5 in close vicinity of the distal end of the tubular body 2. In this structure, by pulling the wires 5 singly, the deformable portion 21 can be bent to four directions to the positions of the wires (up, down, left, and right, for example). Further, by pulling adjacent two wires simultaneously, the deformable portion 21 can be bent in the four directions at 45° with the above four directions. Further, by pulling adjacent two wires simultaneously by different forces, the deformable portion 21 can be bent in any direction between the directions in which the deformable portion 21 is bent by each of the two wires 5.

Since the deformable portion 21 thus can be bent in many directions at will, the area of the inside wall of a tubular organ which can be examined by an endoscope or treated by a medical device inserted through a lumen in the tubular body 2, without manipulation of the tubular body 2 such as turning or pushing or pulling. As the result visual examination and medical treatment can be performed easily in a short time.

Next, the number and disposition of the compression-resisting members 7 are not limited to those shown in the drawings, too, and three or more compression-resisting members may be used. Specifically, the tubular body 2 has two or more lumens extending to the axis of the tubular body and the compression-resisting members is inserted in all the lumens.

Specifically, in a structure using two or more wires, it is preferable to dispose two lumens for compression-resisting members close to each wire lumen with the wire lumen between, in the same manner as in the above embodiment. For example, when the number of wire lumens is four, eight lumens for compression-resisting members are disposed, in pairs of two for each wire lumen.

By this disposition of lumens for compression-resisting members and wire lumens, it is made possible to bend only the deformable portion 21 of the tubular body 2 in many directions without causing the middle portion 22 to bend.

Since the deformable portion 21 thus can be bent in many directions at will, a wider area of the inside wall of a tubular organ can be examined or treated without delicate manipulation of the tubular body 2, and hence visual examination and medical treatment can be performed easily in a short time.

When using a tube for the compression-resisting member main component 71, the same lumen can be used to hold a pull wire and a compression-resisting member by passing a wire through the opening of a compression-resisting member 7. In this structure, only one compression-resisting member is needed for a wire, and hence only one lumen is need for each pair of a wire and a compression-resisting member. For example, when the number of wires is four, the number of lumens needed in this structure is four.

The tubular medical device of this invention can be used as a tubular body of a balloon catheter with a balloon inflated by injection of a fluid, by adding a lumen for infecting a fluid into the balloon.

The tubular medical device of this invention can be applied not only to a tubular device for endoscopic examination, but also to various types of catheters (abrasion catheter, cardiac output measuring catheter, etc.) and various tubular devices (trocar tube, etc.).

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A tubular medical device comprising:
    a tubular body;
    first, second, third and fourth lumens extending almost the entire length of said tubular body and disposed so that the first and second lumens are at different sides of the third lumen with the third lumen between the first and second lumens, and the first and second lumens being closer to the third lumen than to the fourth lumen;
    a first compression-resisting member held in the first lumen and having a distal end positioned a predetermined distance from a distal end of the tubular body toward a proximal side and secured in the first lumen so as not to move in an axial direction of the tubular body;
    a second compression-resisting member held in the second lumen and having a distal end positioned at a predetermined distance from the distal end of the tubular body toward the proximal side and secured in the second lumen so as not to move in the axial direction of the tubular body;
    a wire held in the third lumen and having a distal end secured at a position close to the distal end of the tubular body and displaced from the axis of the tubular body and having a proximal end leading out of a proximal end of the tubular body;

means for pulling the wire disposed at the proximal side of the tubular body and operated to control a direction of a distal end portion of the tubular body by the wire; and the fourth lumen being formed eccentrically to the tubular body at a position spaced from the axis of the tubular body near a circumferential surface.

2. The tubular medical device of claim 1, wherein the fourth lumen extends from the proximal end to a distal end of the tubular body and is open at the distal end of the tubular body.

3. The tubular medical device of claim 1, wherein the first lumen, second lumen and third lumen extend from the proximal end of the tubular body to near the distal end of the tubular body, with distal ends of the first, second and third lumens at a predetermined distance from the distal end of the tubular body toward the proximal side of the tubular body.

4. The tubular medical device of claim 1, wherein the first lumen, second lumen and third lumen are disposed near a circumference of a cross section of the tubular body.

5. The tubular medical device of claim 1, including fiber optics inserted and held in the fourth lumen.

6. The tubular medical device of claim 1, including a tubular reinforcement embedded in a circumferential part of a wall of the tubular body.

* * * * *

UNITED STATES PATENT AND TRADEMARK OFFICE
Certificate

Patent No. 6,595,982 B2                                                    Patented: July 22, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Shin Maki, Kanagawa-ken, Japan.

Signed and Sealed this Sixth Day of December 2005.

NICHOLAS D. LUCCHESI
*Supervisory Patent Examiner*
Art Unit 3763

UNITED STATES PATENT AND TRADEMARK OFFICE
CERTIFICATE OF CORRECTION

PATENT NO. : 6,595,982 B2
DATED : July 22, 2003
INVENTOR(S) : Shin Maki

It is certified that error appears in the above-identified patent and that said Letters Patent is hereby corrected as shown below:

Column 1,
Line 47, insert an opening parenthesis "(" before "Japanese".

Column 2,
Line 50, change "FIG. 8 is a sectional view along line IV-IV in FIG. 6." to
-- FIG. 8 is a sectional view along line VIII-VIII in Figure 6. --.

Column 5,
Line 24, "dosed" should be -- closed --.

Column 7,
Line 23, put a period at the end of the sentence.

Signed and Sealed this

Fourteenth Day of March, 2006

JON W. DUDAS
*Director of the United States Patent and Trademark Office*